United States Patent [19]

Lehn

[11] 4,076,724
[45] Feb. 28, 1978

[54] POLYCYCLIC MACROCYCLIC COMPOUNDS

[75] Inventor: Jean-Marie Lehn, Strasbourg, France

[73] Assignee: L'Agence Nationale de Valorisation de la Recherche (ANVAR), Neuilly-sur-Seine, France

[21] Appl. No.: 295,083

[22] Filed: Oct. 4, 1972

[30] Foreign Application Priority Data

Oct. 15, 1971 France .............................. 71.37116

[51] Int. Cl.$^2$ .................. C07D 498/18; C07D 513/18
[52] U.S. Cl. ............................... 260/338; 260/327 R; 260/340.3
[58] Field of Search ................ 260/338, 327 R, 340.3

[56] References Cited

U.S. PATENT DOCUMENTS 3,531,468  9/1970  Park et al. ............................ 260/239

Primary Examiner—Norma S. Milestone
Attorney, Agent, or Firm—Donnelly, Maky, Renner & Otto

[57] ABSTRACT

Novel polycyclic macrocyclic compounds having four tertiary nitrogen bridgehead atoms and six bridging chains, each of which have not more than twelve directly connecting atoms between each pair of bridgehead nitrogens, said bridging chains being hydrocarbon chains and hetero-substituted hydrocarbon chains having at least one hetero connecting atom selected from the group consisting of oxygen, sulfur, and nitrogen, at least two of said chains being hetero substituted. When admixed with a compatible cation-donor compound, the polycyclic macrocyclic compounds form stable cation-containing macrocyclic complexes which, in turn, can be conveniently dissociated by addition of acid or a quaternizing acid. The novel polycyclic macrocyclics are valuable for use in the same way and for the same purposes as chelating agents.

The polycyclic macrocyclic compounds are prepared by condensation reactions utilizing high dilution techniques, e.g. by condensing a monocyclic macrocyclic having secondary nitrogen bridgeheads with a substituted hydrocarbon di-carbonyl halide followed by reduction of the resulting lactam or, alternatively, by condensing a monocyclic macrocyclic having secondary nitrogen bridgeheads with a substituted hydrocarbon dihalide (or di-sulfonate).

9 Claims, No Drawings

POLYCYCLIC MACROCYCLIC COMPOUNDS

FIELD OF INVENTION

This invention relates to novel compositions of matter and to processes for their preparation.

This invention relates to novel polycyclic macrocyclic compounds, to processes for their preparation, to complexes formed from the novel polycyclic macrocyclic compounds and to processes for the preparation of such complexes.

GENERAL DESCRIPTION OF INVENTION

Polycyclic Macrocyclic Compounds

The novel macrocyclic compounds of this invention include compounds selected from the group consisting of a compound of following formula I:

   I wherein each R is a bridging chain having not more than twelve directly connecting atoms between the two nitrogen atoms to which it is attached, R being a member selected from the group consisting of a hydrocarbon radical having from 2 to 24 carbon atoms, and a radical defined by following formula II:

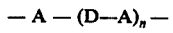   II wherein $n$ is an integer from 1 to 3, each A may be the same or different and is a hydrocarbon having from 2 to 12 carbon atoms; and each D may be the same or different and is a member selected from the group consisting of oxygen, sulfur, and $=N-R'$, $R'$ being a member selected from the group consisting of hydrogen, a hydrocarbon radical having up to 12 carbon atoms, and a hydrocarbonsulfonyl radical having up to 12 carbon atoms; each of said R chains may be the same or different with the proviso that at least two of said R chains is defined by formula II:

the N-oxides of formula I;

the cation-containing-complexes of compounds of formula I and of the N-oxides thereof; and quaternary salts and acid addition salts of compounds of formula I.

Preferred compounds of my invention are those wherein A is ethylene.

The hydrocarbon groups represented by R preferably have from 2 to 20 carbon atoms. Preferred are: straight and branched chained alkylene and alkenylene groups having from 2 to 12 carbon atoms such as ethylene, propylene, butylene and hexylene, heptylene, dodecylene etc. and their unsaturated analogs; cycloalkylene and cycloalkenylene groups such as cyclopropylene, cyclobutylene, cyclohexylene and cycloheptylene and their unsaturated analogs; the corresponding cycloalkylene-di-alkyl groups such as cyclohexylenedimethyl and aromatic groups such as phenylene and phenylene-di-alkyl, preferably phenylene-dimethyl.

The hydrocarbon groups represented by A preferably have from 2 to 12 carbon atoms. Preferred are: straight and branched chained alkylene and alkenylene groups having from 2 to 8 carbon atoms such as ethylene, propylene, butylene and hexylene and their unsaturated analogs; cycloalkylene and cycloalkenylene groups such as cyclopropylene, cyclobutylene, cyclohexylene and cycloheptylene and their unsaturated analogs; the corresponding cycloalkylene-di-alkyl groups such as cyclohexylene-dimethyl and aromatic groups such as phenylene and phenylene-di-alkyl, preferably phenylene-di-methyl. In accordance with the definition the groupings A are chosen so as to provide groupings R having not more than 12 atoms in the direct connection between the two nitrogen atoms to which they are attached.

The hydrocarbon groups and the hydrocarbon-sulfonyl groups represented by $R'$ preferably have from 1 to 12 carbon atoms. Preferred are straight and branched alkyl groups having from 1 to 8 carbon atoms and straight or branched alkenyl groups having from 2 to 8 carbon atoms. Other typical representatives are cycloalkyl, aralkyl and aryl groups. The preferred hydrocarbon-sulfonyl groups are tosyl and benzyl-sulfonyl.

Typical representatives of the groupings R are illustrated below:

A: Hydrocarbon groups represented by R $-CHR'\lambda'$
$-CH_2-$; $-CHR''-CHR''-$; $-CHR''-CH_2-CHR''-$; $-CH_2-CH_2-CHR''-CH_2-(CH_2)_8-$; $-(CH_2)_{12}-$; and unsaturated analogs;

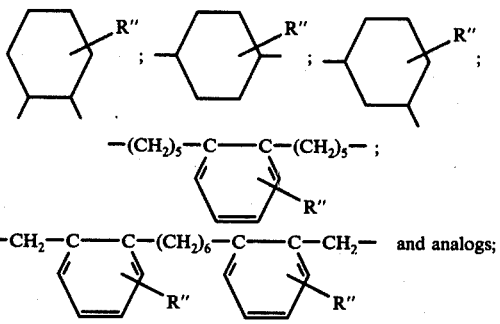

and analogs;

B: The grouping $-A-(D-A)_n-$ represented by the various R groupings.

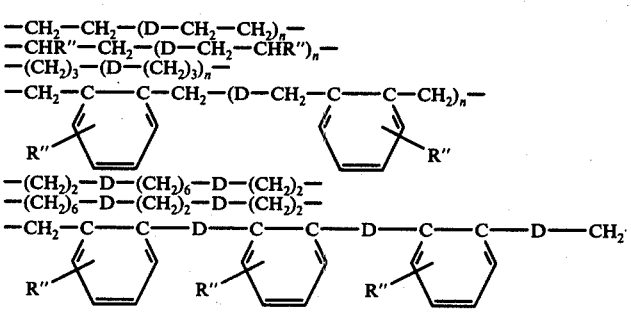

In the above formulae D is as previously defined and R" represents hydrogen or a hydrocarbon group as defined for R'.

The formulae 1 to 10 on the following pages show some typical configurations of the compounds of this invention. Typical representatives of the compounds of this invention may be illustrated by inserting the various definitions of A, R and R' into the formulae 1 to 10. Formulae 11-23 show some of the most preferred compounds. The definitions given above, as well as the formulae 1 to 23 hereinafter make it obvious that the groupings represented by R may be the same or different; that the groupings represented by A may be the same or different and that the groupings or atoms represented by D may be the same or different in the compounds of formula I.
CHART A
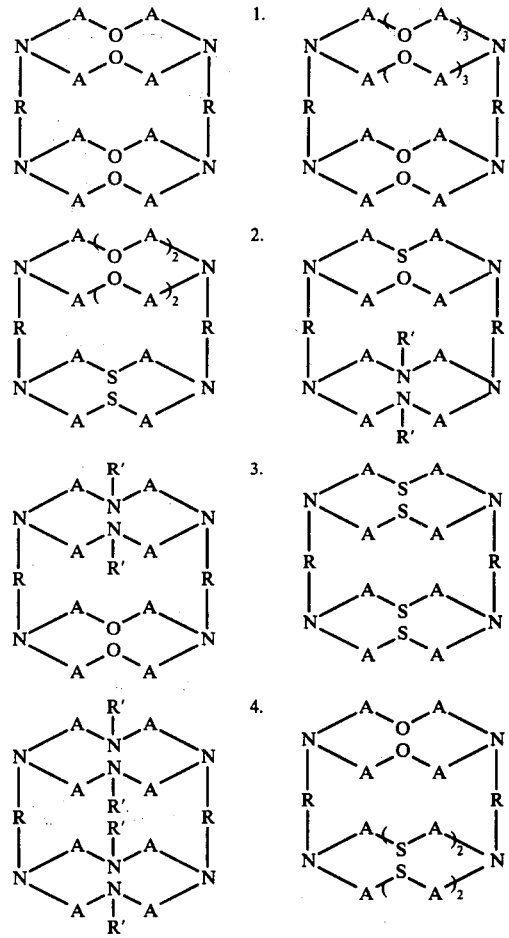
CHART B
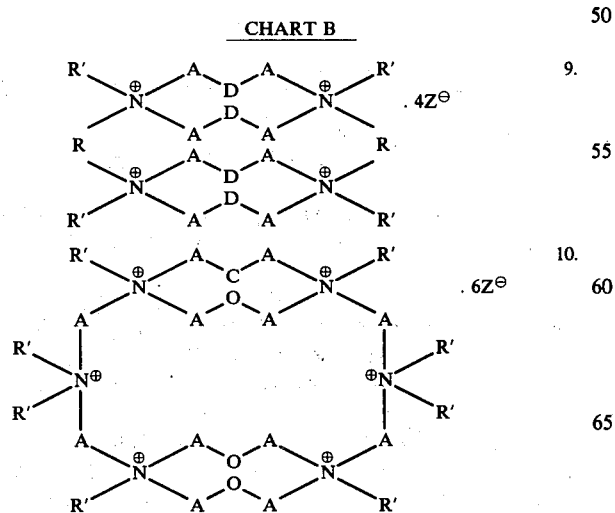
-continued
CHART B
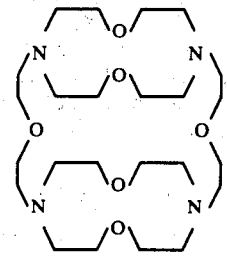
11.
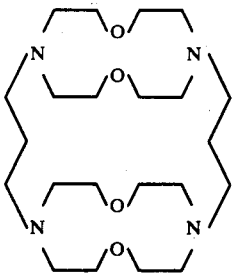
12.
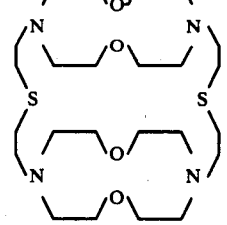
13.
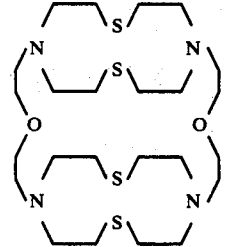
14.
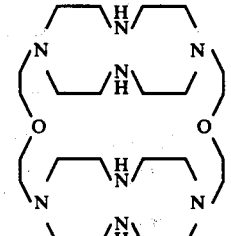
15.
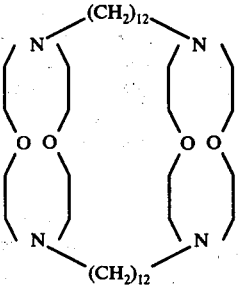
16.

CHART C

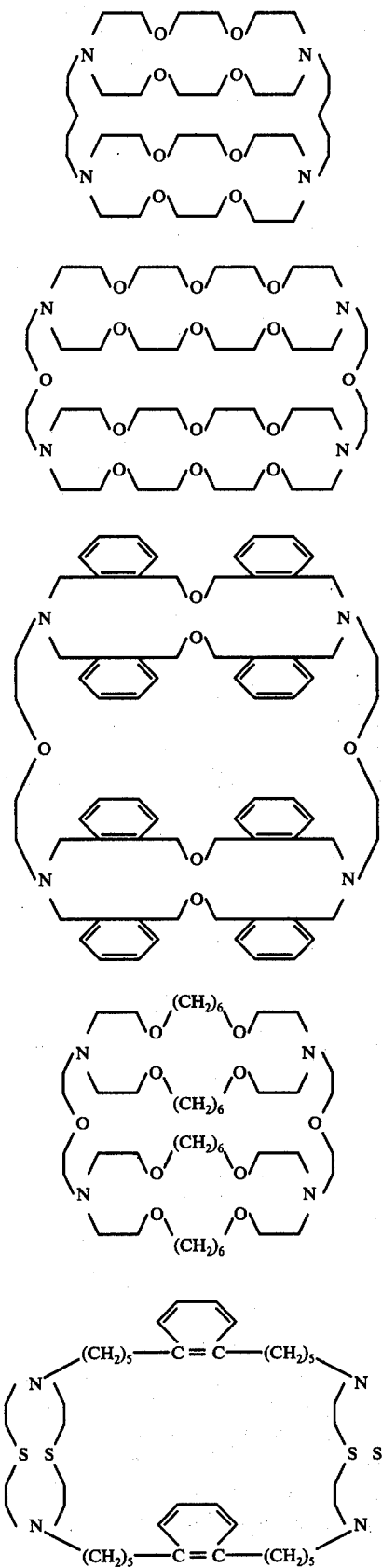

17.

18.

19.

20.

21.

-continued
CHART C

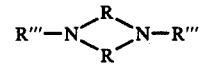
22.

23.

PROCESS FOR PREPARING MACROCYCLIC COMPOUNDS

The compounds of this invention may be prepared by using known chemical reactions. The principle of the processes is either to connect the two monocyclic amines to each other by introducing the two missing R groupings or to introduce one of the groupings R into a molecule in which all other groupings are already present.

One approach for the preparation of this invention is characterized in that a compound of the general formula IV:

$$R'''-N\underset{R}{\overset{R}{\rightleftarrows}}N-R''' \qquad \text{IV}$$

wherein each R is as defined hereinabove and R''' is a member selected from the group consisting of hydrogen, a hydrogenolyzeable group, and a protecting group, with the proviso that only one of the R''' groups can be a protecting group, is reacted with a compound having the following general formula V:

$$Y-R_{(5,6)}Y \qquad \text{V}$$

wherein Y is a member selected from the group consisting of

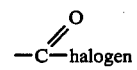

and a leaving group selected from the group consisting of halogen, methanesulfonate and p-toluenesulfonate; and when Y is

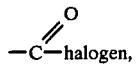

$R_{(5/6)}$ represents a grouping having two carbon atoms less than $R_5$ and/or $R_6$ in a compound of formula I, and when Y is a leaving group, $R_{(5/6)}$ is as defined hereinabove for $R_5$ and $R_6$ in formula I; that any carbonyl group in a so-obtained compound is reduced to $CH_2$; and that, if desired, a compound obtained by any of the previous steps is subjected to one or more of the following finishing steps:
  i. hydrogenolysis of hydrogenolysable groups represented by R'''
  ii. transformation into an ammonium salt;
  iii. transformation into a nitrogen oxide.

The definition halogen comprises all halogen. The preferred hydrogenolysable group is the benzyl group. Various embodiments of this process are described under items A to G below:

A. One embodiment of the above process is characterized in that a compound of the general formula

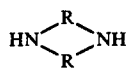  IV wherein R is as previously defined is reacted with a compound of the formula

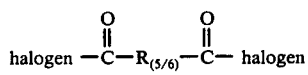  V wherein $R_{(5/6)}$ is a group having two carbon atoms less than the final grouping R followed by reduction of the carbonyl group in the so-obtained compound of the general formula

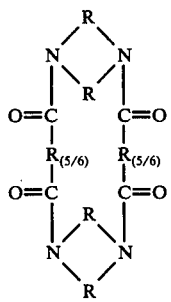  VII (It is obvious that the $R_{(5/6)}$ groups in this formula have two carbon atoms less than the R group of the final compound.)

B. A further embodiment is characterized in that a compound of the formula

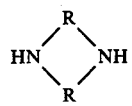  IV wherein R is as previously defined is reacted with a compound of the general formula

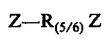  VI wherein $R_{(5/6)}$ is as previously defined and Z is halogen or other good leaving group.

These condensation reactions may be conducted in one single step, as described above, or may involve two or more steps whereby various intermediates formed in the above general processes are isolated before further treatment. By using an excess of the one or the other of the above described reactants various preferred intermediates are obtained which are then further reacted.

C. One variation of the general process is characterized in that the condensation reaction comprises the steps of:
  a. reacting an excess of a compound of the formula IV with a compound of formula V; (For this reaction one may protect one NH, for instance in the form N-Tosyl or N—COOCH$_3$. The protecting group is then removed before step c).
  b. reducing the carbonyl groups in the so-obtained compound of the formula VIII

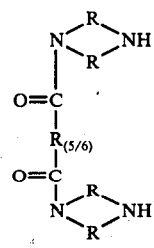  VIII ($R_{(5/6)}$ has two carbon atoms less than the R of the final compound.)
  c. reacting the so-obtained compound of the general formula

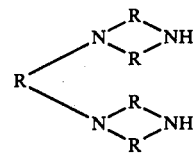  IX with a compound of the general formula V; and
  d. reducing the carbonyl groups in the so-obtained compound of the formula

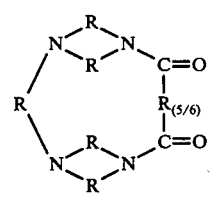  X whereby a compound of formula I is obtained.

D. A further variation is characterized in that the condensation reaction comprises the steps of:
  a. reacting a compound of the general formula IV with an excess of a compound of formula V;
  b. reacting the so-obtained compound of the general formula

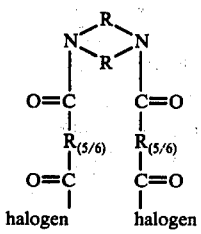 XI (R being a grouping having two carbon atoms less than the final grouping R) with a compound of formula V; and c. reducing the carbonyl groups in the so-obtained compound of the general formula VII whereby a compound of the general formula I is obtained.

E. A further variation of the main process is characterized in that the condensation reaction comprises the steps of:

a. reacting an excess of a compound of the general formula IV with a compound of the general formula VI; and b. reacting the so-obtained compound of the general formula

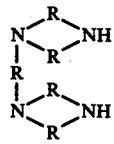 XII with a compound of formula VI whereby a compound of the general formula I is obtained.

F. Still another variant is characterised in that the condensation reaction comprises the steps of:

a. reacting a compound of the general formula IV with an excess of a compound of the general formula VI; and b. reacting the so-obtained compound of the general formula

 XIII

With a compound of the general formula IV whereby a compound of the general formula I is obtained.

G: A variation of process C desribed above is as follows:

a. A compound of the formula

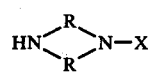

wherein each R is as previously defined and X is a protecting group such as Tosyl or —COOCH$_3$, is reacted with a compound of formula V;

b. The groups X in the so-obtained compound of the formula

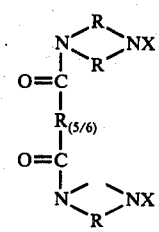 XVI wherein R$_{(5/6)}$ is as previously defined, are then eliminated;

c. The so-obtained compound (X substituted by H in the above formula XVI) is then reacted with compound V;

d. The carbonyl groups in the so-obtained compound of formula

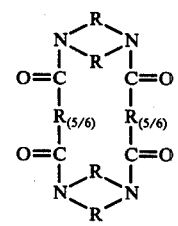 XVII are then reduced to CH$_2$.

If in the above processes monocyclic compounds of the general formula IV wherein R''' represents a hydrocarbon group are used as starting compounds in the reaction with compounds of formula IV then quaternary ammonium salts of the compounds of general formula I are directly obtained.

Naturally a compound obtained according to any one of processes A to F may be subjected, if desired, to one or more of the finishing steps (i), (ii) and (iii) described above.

In order to prevent the formation of polymers, the condensation reactions A and B, as well as reaction C, step (c), reaction D, step (b), reaction E, step (b) and reaction F, step (b) are carried out using high dilution techniques. Any inert solvent may be used, but benzene and toluene are preferred. The acid formed during the reactions A,C (step (c) and D, step (b) must be neutralised. This may be accomplished by using two moles of the diamine to each mole of the halide, or by adding a further base, particularly a tertiary amine such as a trialkylamine or pyridine, preferably triethylamine. The reduction of the carbonyl groups, e.g. in the reactions C, step (b) and (d) and reaction D, step (c) is preferably carried out by means of LiAlH$_4$ or B$_2$H$_6$ in tetrahydrofurane. Other possible reducing agents are mixed hydrides such as for example NaBH$_4$, LiAlH$_3$—OCH$_3$, LiAlH$_3$./AlCl$_3$ and NaBH$_4$/BF$_3$.

The transformation of a compound of formula I into a quaternary ammonium salt or acid addition salt may be accomplished by using standard methods such as reaction with suitable quaternizing agents (e.g. alkyl halides such as methyl iodide) or with a hydrogen halide (e.g. hydrogen chloride) respectively.

Similarly any hydrogenolysable groups may be removed by using standard techniques such as catalytical or electrolytical reduction. Examples of catalysts which may be used are platinum, palladium, rhodium and ruthenium. Preferably, however, the reduction is performed by means of LiAlH$_4$.

Also the transformation of a compound of formula I into its nitrogen oxide may be accomplished by applying standard oxidation procedures such as treatment with excess dilute hydrogen peroxide in water or with perphthalic acid in ether.

Often the immediate product of the above reaction is not the free macrocyclic compound but rather a derivative thereof additionally containing part or all of the structural elements of other constituents of the reaction mixture; in such a case, the macrocyclic compound is subsequently liberated from such derivative, by standard procedures such as for example treatment with dilute acid whereby the acid addition salt of the macrocycle is formed, or with other hydrolyzing agents. Any such salt may be dissolved in water and treated with an anion exchange resin. The so-obtained aqueous solution of the free macrocycle may then be isolated by evaporation to dryness.

A further conceivable process for the preparation of the compounds of this invention comprises introducing one of the groupings of the cyclic amine into a molecule which already comprises all the other groups represented by R.

H. The process is characterized in that a compound of the general formula

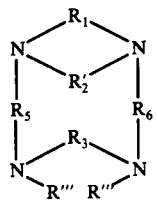   XIV wherein each R and R''' are as above defined. either a grouping $R_2$ or represents a grouping is

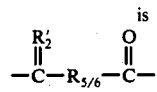

wherein $R_{5/6}$ has two carbon atoms less than the final $R_2$ group is reached with a compound of the general formula

Z—R—Z      XV wherein R and Z are as previously defined; that any carbonyl groups in the so-obtained compound is reduced to $CH_2$; and that, if desired, a compound obtained by any of the previous steps subjected to one or more of the finishing steps (i), (ii) and (iii) described above.

The starting compounds of formula XIV may be obtained according to the following reaction schemes:

CHART D

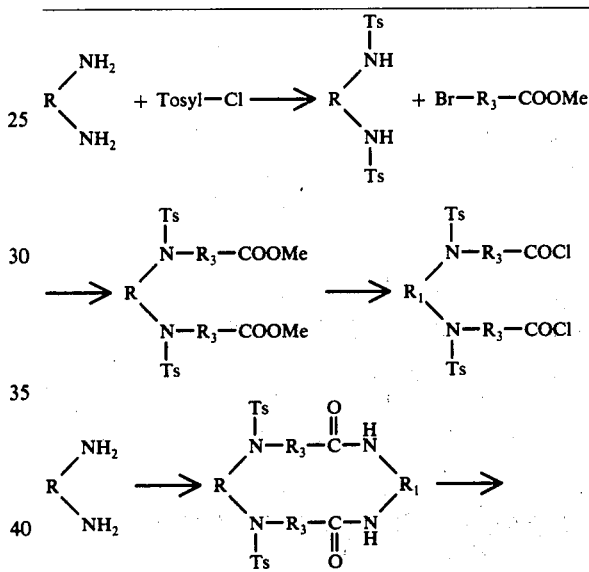

CHART E

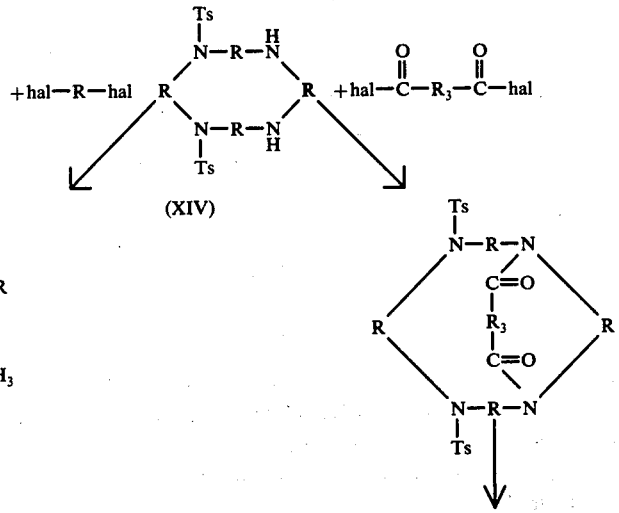

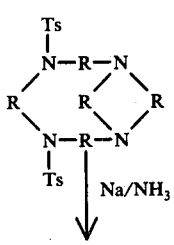

CHART E

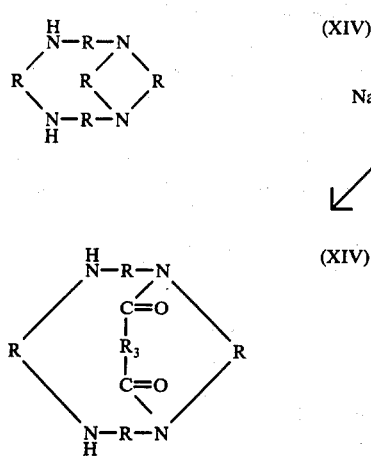
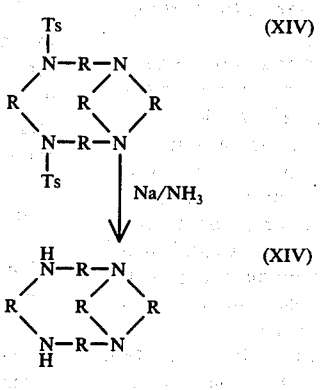

The monocyclic starting compounds of the general formula IV may be obtained according to the processes described in the published German Patent application No. P2028556.7. The starting compounds of formulae V and VI are either known compounds or may be obtained according to standard methods well known in the art.

The compounds of this invention are readily soluble in most common organic solvents and in water.

Like the macrocyclic compounds of the above mentioned German Patent application, the novel macrocyclic compounds have an unusual ability to form stable complexes with compatible cations. It is believed that the various bridges between the nitrogen atoms form a "cage" in which the cation is situated. The ability to form complexes and the stability of the complexes formed seem to depend on the arrangement of the hetero atoms or groups surrounding the cation and on the relative diameters of the cage and the cation. Macrocyclic compounds forming stable complexes with cations of a certain diameter are not able to form complexes with cations having much larger diameters. Generally each macrocyclic molecule is able to form a complex with one cation, although with large systems complexes with two or more cations may be obtained. The magnitude of the charge on the cation has no influence. The cations may be inorganic or organic. In the present compounds selective complexation may be controlled by varying the length of the bridges between the two monocyclic diamines and by varying the size of the monocyclic diamines themselves. The central molecular cavity is of different shape as compared to the earlier bicyclic compounds. The top and bottom of the complex are open and accessible to other ligands. This is of special interest in case of transition metal complexes as their properties may be changed by varying the type of XY ligands. One may also prepare complexes with gases ($O_2$, $N_2$, CO etc.) fixed on the transition metal cation. These differences are the main advantages of the novel macrocycles above previously described macrocycles. The new compounds are of special interest for transition metal or lanthanide cations complexation.

The complexes formed are generally readily soluble in water, $CHCl_3CH_2Cl_2$ and in acetone or other polar solvents, whereas they are slightly soluble or essentially insoluble in non polar organic solvents. They dissociate at a more or less acid pH. Protonation of the free diamine hinders complex formation and leads to the dissociation of the complex by displacement of the equilibrium. The dissociation may be accomplished by treatment with an acid, including Lewis acids. Release of the cation may also be accomplished by treating the complex with a quaternizing agent.

The complexes are normally formed by dissolving the macrocyclic compound and the cation yielding compound in a common solvent, such as for example acetone, methanol or water. The mixture is normally heated approximately to the boiling point of the solvent. If the complex formed is insoluble in the solvent used, the complex will crystallize and may be separated by filtration. If the complex formed is soluble in the solvent used, it may be isolated by evaporating the solution to dryness. The complexes may be purified by recrystallization.

Complexes may also be formed when the cation yielding compound (e.g. the salt) is insoluble in the solvent used. It is sufficient to bring a solution of the macrocyclic compound together with the crystalline salt and agitate the mixture with or without heating.

The formation of complexes is possible even if the cation yielding compound and the complex are insoluble in the medium used. In this case the macrocycle and the cation yielding compound are mixed in the presence of a medium which is then agitated and heated, whereby the crystalline macrocycle gradually changes into the crystalline complex.

The presence of a complex in solution can be determined by spectroscopic analysis, as the addition of the cation causes changes in the spectral patterns of the macrocycle in solution.

The cation complexing properties of the macrocyclic compounds of this invention make them of value for use in much the same way and for the same purposes as chelating agents. Thus, the cation complexing properties of the compounds render them of value in processes directed to the separation of metals, for example, to the separation of metals such as the transition metals and the actinides from low grade sources of these metals and to subsequently obtaining such metals in high purity form. In this connection, the polycyclic, macrocyclic compounds of this invention are considered to be particularly useful in the separation of high cost metals such as those of the platinum group. In the separation of uranium from treated ores, for example, the uranium may be complexed with a polycyclic macrocycle compound and the resulting cation-containing macrocyclic complex subsequently separated by water. Treatment of the uranium-macrocyclic complex with acid will then release the uranium from the complex in the form of a uranium salt.

The compounds of the invention may also advantageously be used for cation transport and for the preparation of ion selective membranes and electrodes The compounds are also of use in chemical syntheses, e.g. in polypeptide and protein syntheses, wherein the compounds advantageosusly selectively protect one of the ammonium cation groups in the amino acid. Additionally, the compounds may be used as a catalyst for ionic reactions in a polar organic media wherein the macrocyclic compounds activate the reaction via an "agent-separated ion pair" mechanism.

The solubility of the complexes of this invention makes it possible to use certain inorganic salts, e.g. of RbCl, CsCl etc. in organic solvents such as chloroform.

When incorporated in various compositions the compounds of this invention "tie-up" trace metals and thus prevent the occurrence of catalytic oxidation due to the presence of trace metals. Additionally, when administered to an animal, e.g. mammals, the compound has an action on biological cation mechanisms such as nervous conduction, sodium-potassium pump, and calcium metabolism of musucle and bone. These compounds are thus useful in conditions in animals requiring the regulation of cation exchange within the host.

The complexes of the transition metals may, as mentioned above, form complexes with various gases. Thus the cobalt complex of compound 12 obtained according to the procedure of Example 10 may form an oxygen complex wherein the oxygen is fixed on the transition metal and is released by heating. Such oxygen complexes may be useful for storage and transport of oxygen (an effect similar to that of hemoglobine). Additionally, the macrocyclic complexes provide convenient means for purifying the macrocyclic compounds per se. Thus, a macrocyclic compound prepared according to the processes discussed hereinabove, which is difficult to purify or separate from by-products, may be converted to a cation containing complex of this invention. Isolation and purification of the complex followed by treatment with acid will yield a purified macrocyclic compound of this invention as the acid addition salt thereof.

The following examples further illustrate the practice of this invention. My invention is not to be construed as limited to the specific embodiments described therein but, rather, to include modifications thereof obvious to those skilled in the art.

EXAMPLE 1

A: Preparation of

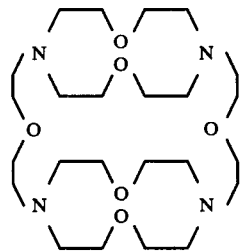
(A)

according to reaction scheme E1A on page 46.

Step (a): This preparation is carried out using the high dilution technique. A solution of 5.1 g. of the diamine and 6.5 g. of triethylamine in 500 ml anhydrous benzene, and a solution of 5.1 g. of diglycolic acid dichloride in 500 ml anhydrous benzene are added dropwise to 1000 ml anhydrous benzene over a period of 10 hours under vigorous stirring. On termination the benzene solution is filtered and evaporated to dryness. The yellow viscous residue is dissolved in chloroform (20 ml). After standing at room temperature for three hours a crystalline material is formed and is filtered off. (The purification may also be accomplished by chromatography on alumina). The crystalline material obtained is the tetramide which crystallizes with two molecules of chloroform m.p. 243° - 246° C.

PMR (D$_2$O): N — CH$_2$ — CH$_2$ — O: 3.2 – 3.9 ppm (broad complex band 32H) — CO — cH$_2$O: 4.3 ppm (broad singlet: 8H).

Mass spectrum: Molecular ion 544.

Step (b): A molar solution of diorane in tetrahydrofurane (20 ml) is added dropwise to suspension of the tetramide (1g) in 15 ml. anhydrous tetrahydrofurane under nitrogen atmosphere at room temperature. The mixture is then refluxed for two hours. The solution is allowed to cool to room temperature and 2 ml. of water are added dropwise. The solution is evaporated to dryness. The intermediate amine-borane is not isolated but treated with 6N hydrochloric acid (25 ml) and refluxed until dissolution is complete. The solution is evaporated to dryness under vacuum and the residue is taken up in minimum amount of water (5 ml). The solution is passed over a column of anion exchange resin (Dowex 1) in its OH form. The column is washed with water until no further basic reaction is observed. The combined aqueous eluates are evaporated to dryness and the residue slowly crystallizes. The product obtained is the title compound which may be purified by extraction with hexane and evaporation to dryness. The residue crystallizes on standing and is analytically pure title compound. m.p. 49°–52° C; yield: 90%

PMR (CDCl$_3$): N—CH$_2$—: 2.7 ppm (two overlapping triplets: 24H); O—CH$_2$—:3.6 ppm (triplet: 24H).

Mass Spectrum: Molecular ion: 488

B. Preparation of

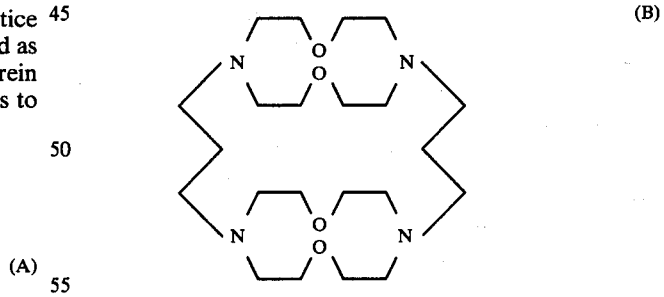
(B)

according to rection scheme E1B on page 46. By following the above process using as a diacidhalide the compound ClCO — CH$_2$ — COCl the title compound is obtained:

NMR(COCl$_3$): —CH$_2$—CH$_2$—CH$_2$—: broad band at 1.4–1.8 ppm: N—CH$_2$: 2.5–3 ppm: triplet + broad band: O—CH$_2$: 3.4–3.9 ppm, several peaks.

EXAMPLE 2

Preparation of (A) according to reaction scheme E2 on page 46. Step (a): 0.01 mole of diglycoloic acid dichloride in benzene are added to a large excess of the diamine dissolved in benzene and the so-obtained diamide is isolated.

Step (b): The diamide from step (a) is dissolved in anhydrous tetrahydrofurane and slowly added to a mixture of tetrahydrofurane and LiAlH₄ while stirring and heating at the reflux temperature. After the addition is completed, the mixture is stirred under reflux and under a nitrogen atmosphere for 24 hours. After cooling to room temperature the excess reagent is destroyed by adding a mixture of water and tetrahydrofurane (1:2). The mixture is filtered and the filtrate evaporated to dryness. The desired product may be purified by chromatography on alumina.

Step (c): Following the procedure described in step (a) of Example 1 a solution of the tetramine obtained above in benzene is treated with a solution of diglycolic acid dichloride under high dilution conditions.

Step (d): The diamide obtained in step (c) is reduced to the desired product with diborane, following the procedure described in step (b) of Example 1.

EXAMPLE 3

Preparation of (A) according to reaction scheme E3 on page 47. Step (a): 0.01 mole of diethyleneglycol dibromide in benzene are added to a large excess of the diamine dissolved in hot benzene or toluene and the so-obtained tetramine is isolated.

Step (b): Equimolecular solutions of the tetramine obtained according to step (a) and diethyleneglycol dibriomide in toluene are added to boiling toluene while stirring (high dilution conditions). After evaporation to dryness and purificiation by chromatography on alumina the desired tetramine is obtained.

EXAMPLE 4

Preparation of

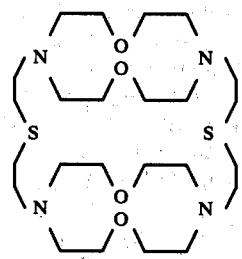

(C)

according to reaction scheme E4 on page 47. By following the procedure of Example replacing the diglycolic acid dichloride in step (a) by thiodiglycolic acid dichloride the title compound is obtained.

EXAMPLE 5

Preparation of

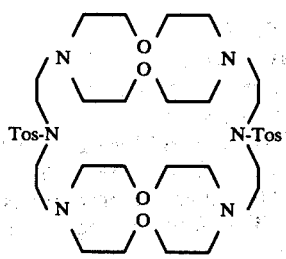

(D)

according to reaction scheme E5 on page 48.

The procedure of Example 1 steps (a) and (b) are used, except that because of the low solubility of the above described tetramide the reduction in step (b) is performed in hot tetrahydrofurane. The tetramide dissolves progressively in the course of the reduction. The tosyl groups may be eliminated by treatment of the tetramine ditosylamide with sodium in liquid NH₃.

EXAMPLE 6

According to the procedure of Example 1 the following compound is prepared (see reaction scheme E6 on page 48.

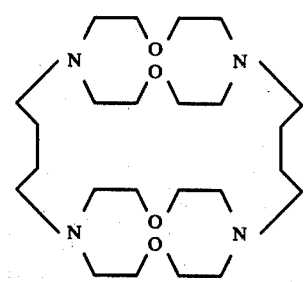

(E)

EXAMPLE 7

Preparation of

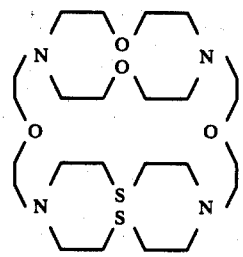

(F)

according to the reaction scheme E7 on page 48.

Step (a) The reaction is performed following the procedure of step (a) of Example 2, except that the diamine is added dropwise to an excess of dichloride.

Step (b) The step follows the procedure of step (c) of Example 2, except that here the dichloride obtained according to step (a) is reacted with the diamine and that a different diamine than in step (a) is used.

Step (c) The reduction follows the procedure described under Example 1, step (b).

EXAMPLE 8

Preparation of

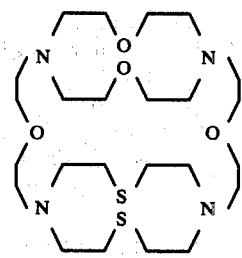

(G)

according to reaction scheme E8 on page 49.

Step (a) The diamine in benzene is added to an excess of diethylenglycol dibromide in hot benzene.

Step (b) Equimolecular solution of the dibromide obtained according to step (a) and the second diamine in toluene are added to boiling toluene while stirring (high dilution conditions). After evaporation to dryness and purification by chromatography on alumina the desired tetramine is obtained.

EXAMPLE 9

Preparation of

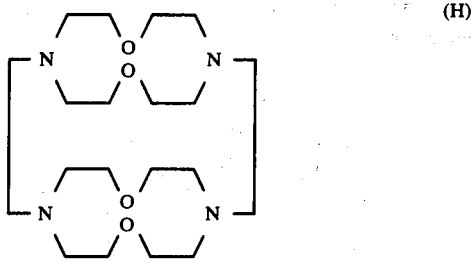
(H)

according to reaction scheme E9 on page 49.

Step (a) The diamine is reacted with Tosyl-Cl.

Step (b) The tosylated diamine is reacted with Br—CH$_2$.COOMe.

Step (c) The diester obtained in step (b) is hydrolysed and the free diacid and is transformed into the dihalide.

Step (c) The dihalide is reacting with a further amount of starting compound applying the high dilution technique.

Step (e) The dicarbonyl compound obtained in step (d) is reduced by means of LiAlH$_4$.

Step (f) The so-obtained tetramine in which two of the amino groups are blocked by tosyl groups is further reacted with

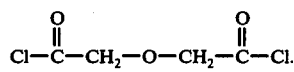

Step (g) By treating the compound obtained according to step (f) with metalic sodium in liquid ammonia the tosyl groups are eliminated.

Step (h) The so-obtained diamine is further reacted with Cl—CO—CH$_2$—O—CH$_2$—CO—Cl.

Step (i) By following the procedure of step (b) of Example 1 the carbonyl groups in the compound obtained in step (h) are reduced and the desired compound obtained.

By following the appropriate procedure of one of the processes of Examples 1 to 9 the compounds 11 to 22 shown on page 10 may be obtained.

EXAMPLE 10

Preparation of CsCl complex or compound A

An excess of solid CsCl is added to a chloroform solution of compound A (obtained according to Example 1A). The CsCl slowly dissolves as the complex is formed. After about 30 minutes the solution is filtered and ether is added until the solution becomes slightly cloudy. The solution is stored in the refrigerator at about 0° C. Crystals or the 1/1 complex of the tetramine A with CsCl are obtained.

PMR (CDCl$_3$): 2.6 - 2.9 ppm (multiplet: 24H.); 3.4 - 3.8 ppm (triplet: 24H).

Following the procedure outlined above, complexes of compound A have been made with the following salts:

| CsSCN | RbCl |
| CsI | Ba(SCN)$_2$ |
| CsCl | |

½ complexes of A with two Ag$^+$ respectively two Tl$^+$ cations have also been prepared.

EXAMPLE 11

Preparation of a Co(SCN)$_2$ complex of compound B

A methanol solution or Co(SCN)$_2$ is added to a methanol solution of compound B (obtained according to Example 1B). A reddish-violet cobalt comples precipitates and is filtered off m.p. 288°-290° C.

EXAMPLE 12

By treating the complexes obtained according to Examples 10 and 11 with dilute hydrochloric acid the respective chlorides are formed with the various cations and the macrocyclic compound may be obtained in free form as the hydrochloride salt.

EXAMPLE 13

Preparation of

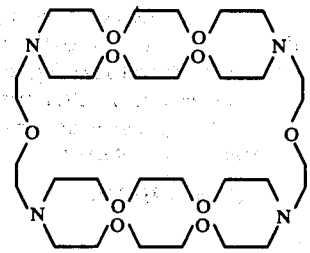

according to reaction scheme E13 on page 50.

Step (a): 3.3 g of compound (2) is added to 5 g. of compound (1) in 200 cm$^3$ of benzene in the presence of 8 g. triethylamine. The resulting mixture is extracted first with distilled water, to remove unreacted compound (1), followed by an extraction with aqueous acid removing compound (3) from the mixture. This fraction is made basic and extracted with CHCl$_3$. Upon removal of the solvent 3.6 g. of compound (3) is obtained. It is purified by chromatography on Al$_2$O$_3$. The product is a viscous oil. (Yield 50%)

Step (b): A solution of 0.59 g. of compound (4) in 100 ml. dry benzene is added to a solution of 2.5 g. of compound (3) and 2 g. of ethylamine in 100 ml. dry benene. After the reaction is finished the mixture is washed with 20 ml NaOH solution (10%)
20 ml. aqueous acid (1 n)
and
3 × 20 ml. distilled water.

The benzene phase is dried with Na$_2$SO$_4$ and evaporated. 2.8 g. of compound (5) are obtained.

Step (c): The crude compound (5) is treated with 20 ml. of a mixture of AcOH/HBr during 3 h. 80 ml. water is then added and the mixture is extracted with CHCl$_3$. The mixture is made basic and is again extracted with CHCl$_3$. After drying the mixture extracts with Na$_2$SO$_4$ and evaporation of the solvent 1.8 g. of compound (6) are obtained. Viscous oil. Yield 90-95%.

Step (d): This step is performed using high dilution technique. A solution of 4.3 g. of compound (6) and 3 g. of triethylamine in 500 cm³ anhydrous benzene is added dropwise to a solution of 1.2 g of compound (4) in 500 cm³ anhydrous benzene. After the reaction is completed the benzene solution is evaporated to reduce the volume and the rest is filtered through Al₂O₃ column. The product is eluated from the column by means of CHCl₃. The CHCl₃ is evaporated, the residue recrystallised from nitromethane and compound (7) having a m.p. of 185°–186° C is obtained. Yield 65%.

Step (e): To a solution of 3 g. of compound (7) in 30 cm² anhydrous tetrahydrofurane are added 60 cm³ of a molar solution of B₂H₆ in anhydrous tetrahydrofurane. The mixture is heated 15 h. at reflux after which time the solvent is evaporated. The white substance obtained is extracted with CHCl₃ and the extract is filtered. The CHCl₃ is evaporated and the residue is heated with HCl (6N) 6 h. at 90° C. The solution is then extracted with CHCl₃, and the water phase is made basic and extracted once more with CHCl₃. The CHCl₃ extracts are mixed, dried with Na₂SO₄, evaporated and kept under vacuum 20 h. at 60° C. The product, Compound I, is recrystallised from heptane M.P. 64° C Yield 95%.

NMR: broad triplet at 2.8 ppm (CH₂N protons) broad tripelt at 3.5 ppm (CH₂O protons) singlet at 3.6 ppm (OCH₂CH₂O).

EXAMPLE 14

Preparation of

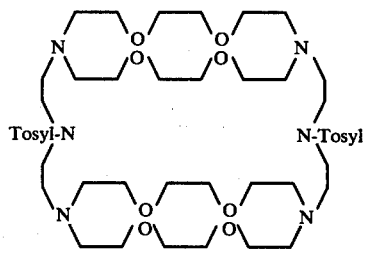

By following the procedure of Example 13 but replacing the diglycolic acid dichloride (4) of Example 13 by the dichloride of the formula

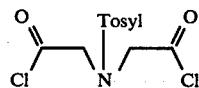

the above compound is obtained. M.P. 152° C.

E1A:

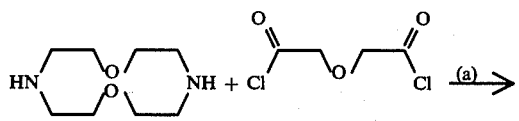

-continued

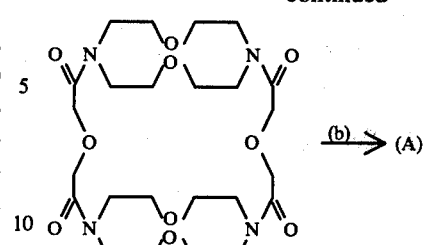

E1B:

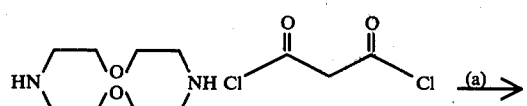

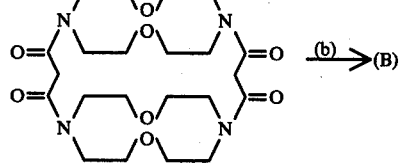

E2:

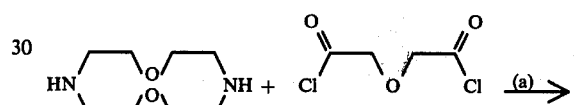

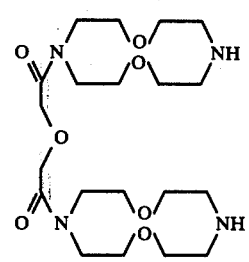

Chart F

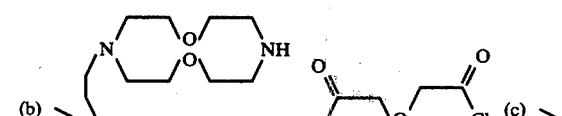

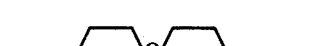

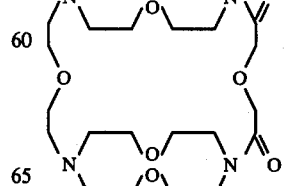

E3:

-continued
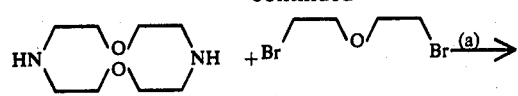
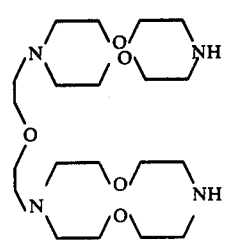
E4:
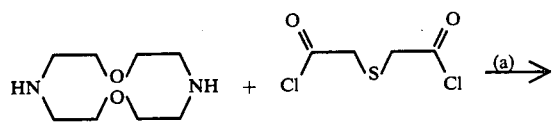
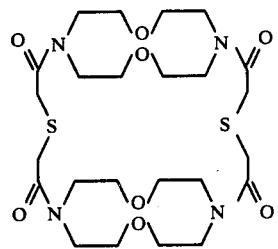
Chart G
E5:
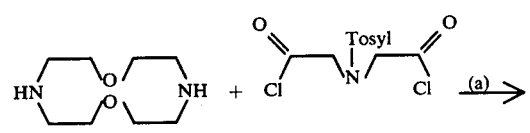
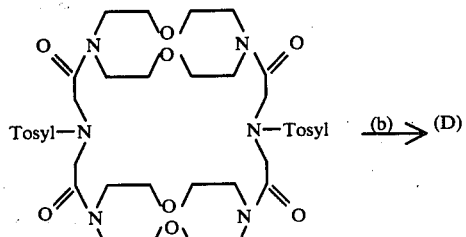
E6:
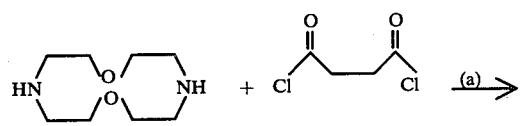
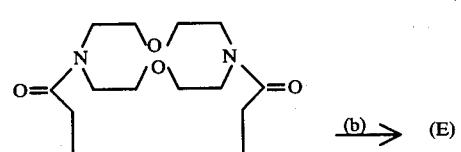
E7:
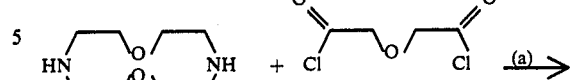
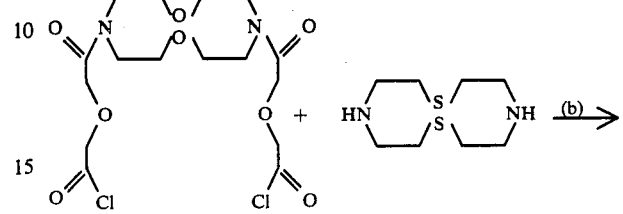
Chart H
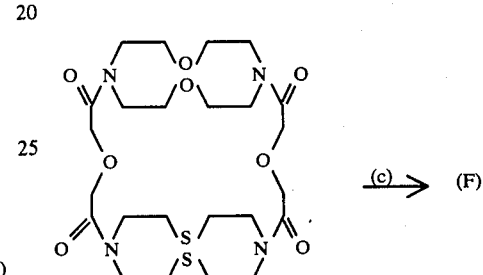
E8:
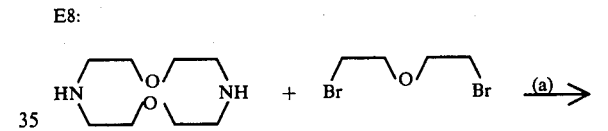
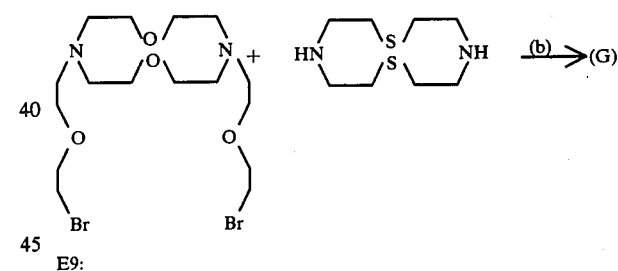
E9:
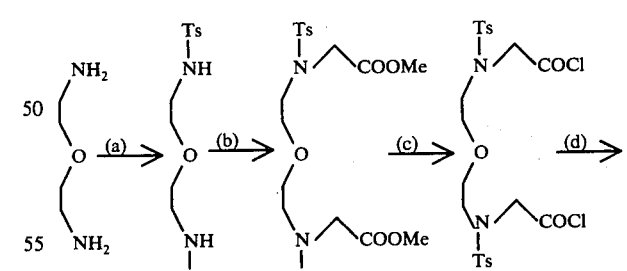
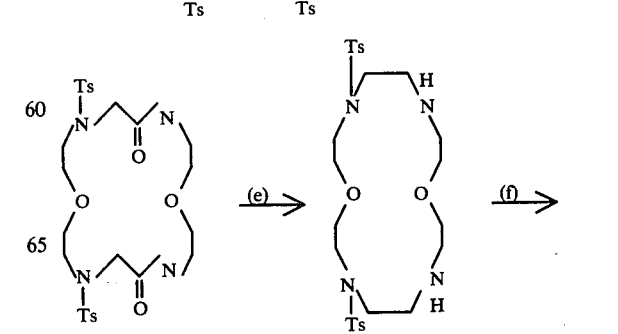

-continued
Chart I
5
K
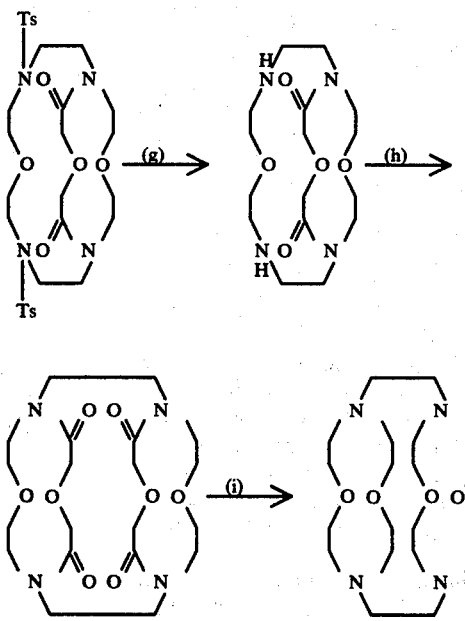
E. 13:
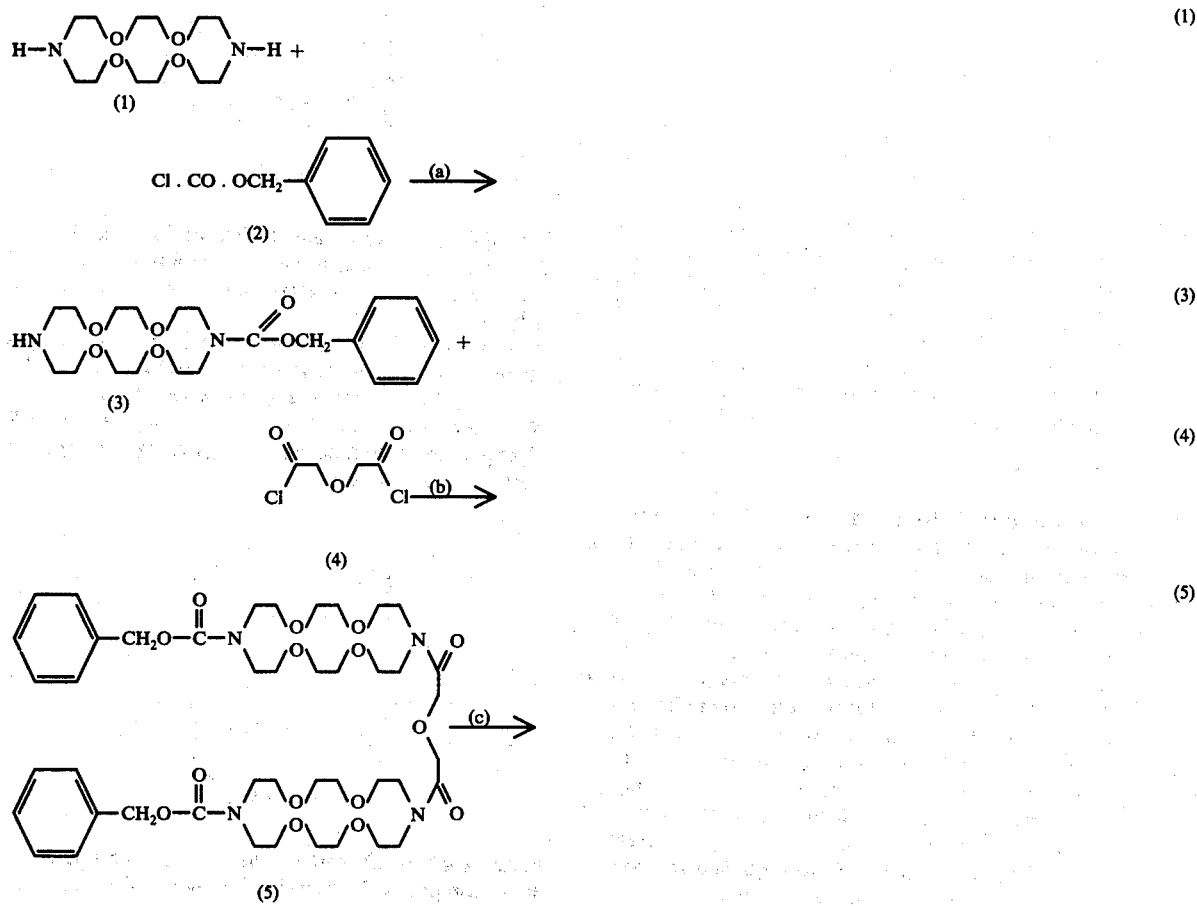

-continued

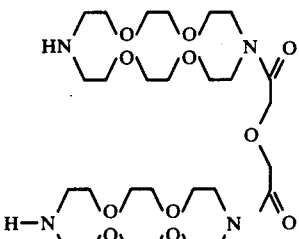

(6)

Chart K

E. 13: (Cont.)

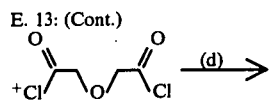

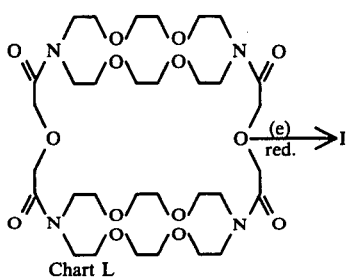

Chart L

I claim:

1. A polycyclic macrocyclic compound selected from the group consisting of a compound of the following formula I:

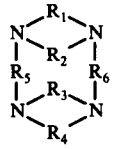

I wherein each R is a bridging chain having not more than twelve directly connecting atoms between the two nitrogen atoms to which it is attached and having a saturated carbon atom directly connected to each of said nitrogen atoms, R being a member selected from the group consisting of a hydrocarbon radical having from 2 to 24 carbon atoms, and a radical defined by following formula II:

$$-A-(D-A)_n-$$

II wherein n is an integer from 1 to 3, each A may be the same or different and is a hydrocarbon having from 2 to 12 carbon atoms; and each D is a member selected from the group consisting of oxygen, sulfur, and $=N-R'$, $R'$ being a member selected from the group consisting of hydrogen, a hydrocarbon radical selected from the group consisting of a straight and branched alkyl group having from 1 to 8 carbon atoms and a straight and branched alkenyl group having from 2 to 8 carbon atoms, and a hydrocarbonsulfonyl radical having up to twelve carbon atoms, each D may be the same only when D is oxygen, or sulfur; ech of said R chains may be the same or different with the proviso that at least two of said R chains are defined by formula II and when $R_5$ and $R_6$ are defined by formula II, the integer n is 1;

and with the proviso that the number of both the carbon and hetero directly connecting atoms in $R_2$, $R_3$ and $R_4$ is the same as in $R_1$, and all the hetero atoms in $R_2$, $R_3$ and $R_4$ are spaced symmetrically with the hetero atoms in $R_1$; and the number of both the carbon and hetero directly connecting atoms in $R_5$ is the same as $R_6$, any hetero atom in $R_6$ being spaced symmetrically with any hetero atom in $R_5$.

2. A compound according to claim 1 wherein each of $R_1$, $R_2$, $R_3$ and $R_4$ is defined by formula II, said compound having the following general formula:

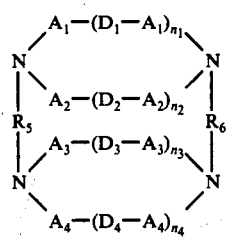

wherein A, D, R and n are as defined in claim 1.

3. A polycyclic macrocyclic compound of claim 1 which is a compound of formula I therein wherein A is ethylene.

4. A polycyclic macrocyclic compound of claim 1 wherein A is ethylene, D is oxygen, sulfur, or $=N-R'$, $R'$ being hydrogen, tosyl, and benzenesulfonyl.

5. A compound according to claim 1 wherein each R bridging chain is defined by formula II, said compound having the following general formula:

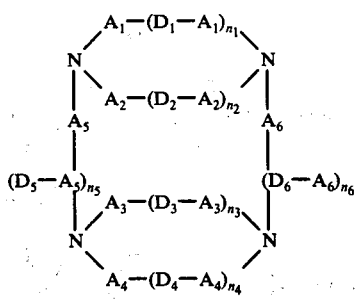

wherein each A, D, and n is as defined in claim 1.

6. A compound having the following formula:

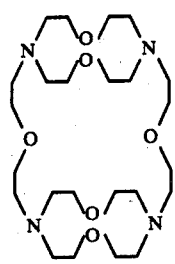
7. A compound having the following formula:
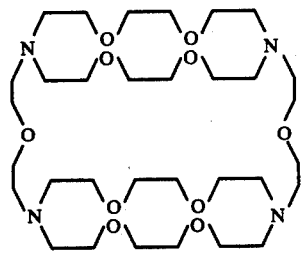
8. A compound having the following formula:
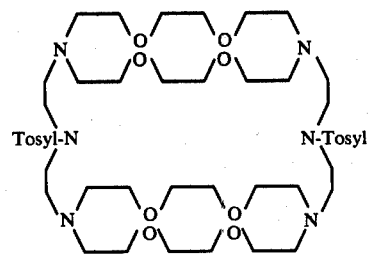
9. A compound having the following general formula:
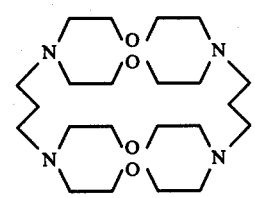
* * * * *